United States Patent [19]

Youdelis

[11] 4,039,329

[45] Aug. 2, 1977

[54] DENTAL POWDER COMPOSITE AND AMALGAM

[76] Inventor: William V. Youdelis, 1935 W. Grand Boulevard, Windsor, Ontario, Canada

[21] Appl. No.: 586,822

[22] Filed: June 13, 1975

Related U.S. Application Data

[63] Continuation-in-part of Ser. No. 551,572, Feb. 20, 1975, abandoned.

[51] Int. Cl.² ............................................. C22C 5/06
[52] U.S. Cl. .................................... 75/169; 75/134 T; 75/173 R; 75/173 C; 75/255
[58] Field of Search .............. 75/0.5 R, 134 T, 173 R, 75/173 C, 169

[56] References Cited

U.S. PATENT DOCUMENTS

| | | | |
|---|---|---|---|
| 3,305,356 | 2/1967 | Youdelis | 75/134 |
| 3,495,972 | 2/1970 | Baum | 75/0.5 |

*Primary Examiner*—L. Dewayne Rutledge
*Assistant Examiner*—E. L. Weise
*Attorney, Agent, or Firm*—Stevens, Davis, Miller & Mosher

[57] ABSTRACT

A dental powder composite adapted to be combined with mercury to form dental amalgam is disclosed which comprises amalgamatable silver-tin alloy in powder form and unalloyed indium powder. Amalgamation of this composite may be achieved with less mercury than used with prior composites and results in an amalgam having improved mechanical properties.

26 Claims, No Drawings

DENTAL POWDER COMPOSITE AND AMALGAM

REFERENCE TO RELATED APPLICATION

This application is a continuation-in-part of my U.S. application Ser. No. 551,572, filed Feb. 20, 1975, now abandoned

BACKGROUND OF THE INVENTION

This invention relates to dental powder composites and more particularly to such composites adapted to be combined with mercury to form dental amalgam and to such amalgams.

Commercial dental alloys are generally supplied in powder form or in loosely compressed tablets of alloy powder material. The powder or tablet form is combined with mercury (trituration procedure) to form the amalgam which is used for filling of dental cavities. In general only sufficient mercury is used to provide the required plasticity to permit packing of the amalgam into the cavity. The plasticity of the amalgam is dependent upon several factors including the composition of the alloy, the particle size of the powders and trituration mode (time and energy input). For most commercial dental alloys the mercury to alloy weight ratios recommended for trituration fall in the range of 1:1 to 1.6:1.

It has now been well established that the mechanical properties of the dental amalgam deteriorate as the residual mercury content increases. Mahler and Van Eysden in the Journal of Dental Research, 1969, Vol. 48, No. 4, page 501, have shown that the properties of dynamic creep, static creep, ADA flow, 1 hour and 7 day compressive strengths as well as 7 day tensile strength of the amalgam are all significantly poorer when the residual mercury content of the amalgam increases from 48% to 53%. Further, Mateer and Reitz in the Journal of Dental Research, 1970, Vol. 49, No. 2, page 399, have shown that the principal mechanism in amalgam corrosion is the breakdown of the tin-memory phase (gamma-2), the formation of such phase being increased in the amalgam by the presence of excess liquid mercury during trituration as shown by Gaylor in the Journal of the British Dental Association, 1936, Vol. 60, page 11. These various investigations clearly show that to attain optimum serviceability from amalgam restorations a minimum effective amount of mercury should be employed for trituration in developing the desired plasticity. On the other hand, it is also necessary that sufficient mercury be used to provide the desired plasticity; total elimination of mercury as taught by Baum, U.S. Pat. No. 3,495,972 is seen to be undesirable because of the lengthening of the setting time which results.

It is recognized that the addition of many metals, including indium, to dental amalgam has been known in the prior art, as shown for example in Gray, U.S. Pat. No. 1,959,668; Gray, U.S. Pat. No. 1,963,085; Beldham, U.S. pat. No. 3,554,738; and Muhler, U.S. Pat. No. 3,676,112. But all these patents teach either the alloying of the indium with the silver-tin alloy or the combination of indium with mercury prior to the amalgamation of the silver-tin alloy. None teaches combination of unalloyed indium powder with the silver-tin alloy prior to amalgamation thereof. Even my own U.S. Pat. No. 3,305,356, which teaches that indium may be alloyed with silver and other metals to form dental alloy, does not teach the addition of unalloyed indium powder to the silver-tin alloy.

It has now been discovered that the addition of discrete particles of unalloyed indium to silver-tin alloy prior to amalgamation substantially reduces the deleterious gamma-2 phase and allows trituration with less mercury than known in the prior art, thus resulting in a mechanically stronger dental amalgam.

An object, therefore, of this invention is to provide a dental alloy powder to attain improved properties of the formed dental amalgam.

A further object of this invention is to provide a dental alloy powder which substantially decreases the amount of mercury required for amalgamation and hence reduces the residual mercury content of the amalgam.

SUMMARY OF THE INVENTION

I have found that when unalloyed indium powder is admixed into dental alloy powders to make a dental powder composite, and the amalgam is formed, the mercury to composite weight ratio may be decreased to approximately one-half that required for most commercial dental alloys marketed. Mercury to composite weight ratios of 0.5:1 to 0.75:1 are sufficient for trituration and provide the required degree of initial plasticity for the amalgam. Higher mercury to composite weight ratios may be employed; however the amalgam properties will in general deteriorate if the optimum amount of mercury is exceeded, particularly if condensation is poor. The preferred weight ratio of mercury to powder composite in the amalgam of the invention is therefore from about 0.5:1 to about 1:1, the most preferred weight ratio is from about 0.5:1 to about 0.75:1.

In addition to reducing the amount of mercury required for trituration I have further found that the deleterious gamma-2 phase is substantially reduced or virtually eliminated depending on the amounts of indium and mercury employed. The reduction in the amount of mercury with the resultant decrease or elimination of the gamma-2 phase is reflected in substantially higher compressive strengths being obtainable in the formed amalgams.

The above mentioned improved amalgam properties are obtained when indium is incorporated into the amalgam as a powder addition to commercial-type dental alloy powders, forming a powder composite and amalgamating with mercury in the conventional manner. The indium may contain additional elements or impurities provided these do not significantly decrease the high affinity for amalgamation that is characteristic of indium, and which is an essential requirement in this invention.

Thus according to one aspect of this invention there is now provided a dental powder composite comprising (a) about 70% to 99.5% by weight of an amalgamatable alloy in powder form, containing about 75% by weight silver and about 25% by weight tin, the alloy having up to 8% by weight of the silver-tin alloy replaced by up to 6% by weight of copper and up to 2% by weight of zinc and (b) about 0.5% to about 30% by weight of indium powder. The amalgamatable alloy powder employed in the present invention, which contains silver and tin and optionally copper and/or zinc may also contain additional elements or impurities of non-essential characteristics.

The indium powder should be of a particle size which may readily react and dissolve in the mercury during trituration before significant amalgamation of the other constituents of the powder composite occurs. The decreased affinity and rate of amalgamation of the other constitutents in the powder composite results in the amalgam developing a higher initial plasticity for lower mercury contents. The optimum particle size of the indium powder will depend on the energy input during trituration and a particle size of below about −200 mesh has been found to be adequate in most cases. The powdered indium may be prepared from ingots of the metal using any of several well known atomization methods.

It is an essential feature of the present invention that the powder composite be formed prior to the addition of the mercury for amalgamation, for the improved properties and beneficial effects of the subsequently formed amalgams can be obtained only if indium is admixed as a constituent powder into the dental powder composite. I have found that little or no beneficial effects are imparted to the amalgam if the indium is introduced as an alloying component in one of the constituent alloy powders or in the mercury prior to trituration. The reason for this behaviour is not completely understood, although it is probable that in the former insufficient indium is released during trituration to impart sufficient plasticity to the amalgam with the lower mercury additions recommended, while in the latter insufficient amalgamation occurs (even when trituration is prolonged) due to the low reactivity of the indium-mercury amalgam.

I have found that there is an optimum amount of indium that may be incorporated into the dental powder composite below and above which the beneficial effects in the subsequently formed amalgam are diminished. The optimum amount of indium may vary from about 5% to about 15% by weight depending upon the composition of the alloy, particle size and distribution, and the energy imput during trituration, and is preferably on the order of about 10% by weight. The setting rate of the amalgams, as indicated by the 1 hour compressive strength, generally decreases with increase in indium content; however, this may be offset to some extent by employing a finer particles size for the powder composite and thereby increasing the amalgamation rate. This decrease in setting rate with increase in indium content is also indicative of the necessity for the inclusion of mercury in the amalgam of the invention. If no mercury is used, the setting time increases to several days or more.

The beneficial effects and improved amalgam properties resulting on admixing indium powder is most striking with dispersion-type amalgam filling materials such as disclosed in my U.S. Pat. No. 3,305,356, issued Feb. 21, 1967. I have found that when the indium and the dispersion phase are within certain narrow concentration limits in the dental powder composite an exceptionally high compressive strength, in conjunction with a moderate to high setting rate, is obtained in the amalgam using the recommended low mercury to composite ratio for trituration. Thus according to another apsect of this invention there is now provided an indium-containing, dispersion-type dental powder composite, which requires for trituration a mercury to composite ratio less than 1:1 and preferably from about 0.5:1 to about 0.75:1, the resulting amalgam filling material exhibiting a considerably improved compressive strength, said dental powder composite comprising: (a) about 45% to 50% and preferably about 48% by weight of an amalgamatable alloy containing about 75% by weight silver and 25% by weight tin, the amalgamatable alloy having up to 8% by weight of the silver-tin alloy replaced by up to 6% by weight copper and up to 2% by weight zinc, (b) about 40% to 45% and preferably about 42% by weight of a dispersion phase silver-base alloy containing at least 50% by weight silver, and (c) about 8% to 12% and preferably 10% by weight of indium. The amalgamatable alloy, dispersion phase alloy, and indium are added as constituent powders, for which the particle sizes are at least −325 mesh, and are thoroughly mixed and blended to form the dental powder composite. The dispersion phase alloy which may be used in this invention is any silver base alloy containing 50% by weight or more of silver, and preferably a silver-copper alloy in which the copper is less than 50% by weight and preferably about 28% by weight.

The following examples are given solely for the purpose of illustrating the present invention. The powder composites were prepared by mixing essentially pure indium powder having a particle size of about −325 mesh with the commercial type alloy powders and the mixture subsequently amalgamated with mercury in the conventional manner.

EXAMPLE I

This example was carried out to determine the variation in the amount of gamma-2 phase in the formed amalgam when the indium and mercury contents are varied. A conventional type, silver-tin base alloy powder was used in the preparation of the powder composite samples. This alloy powder was used alone for samples having no indium and was admixed with indium powder prior to trituration for samples containing indium. The amalgams were prepared by triturating the powder composite samples for 20 seconds employing a low energy input amalgamator, condensing the amalgam at 10,000 psi and aging for 5 days at room temperature.

The analyses of the amalgam specimens were performed using an X-ray diffraction (copper Kα radiation, nickel filter) technique. The relative amounts of gamma-2 phase were determined from the characteristics reflections corresponding to the (10.1) and (00.1) planes of the closed-packed hexagonal crystal structure of gamma-2. The amalgam containing no indium and triturated with a mercury to composite weight ratio of 1.6:1 exhibited the largest amount of gamma-2 phase. The intensity of the gamma-2 reflection for this amalgam was arbitrarily affixed a value of 100 as the standard against which the other amalgam specimens were compared.

| Sample No. | Weight Indium % | Mercury to Composite Weight Ratio | Relative Amount gamma-2 |
|---|---|---|---|
| 1 | 0 | 1.6:1 | 100 |
| 2 | 0 | 1:1 | 50 |
| 3 | 5 | 0.75:1 | 30 |
| 4 | 10 | 1:1 | 70 |
| 5 | 10 | 0.75:1 | 30 |
| 6 | 10 | 0.5:1 | 15 |

The above data show that the amount of gamma-2 phase is strongly dependent on the amount of mercury which is used for amalgamation and such phase may be substantially reduced or virtually eliminated by appropriate additions of indium which permits corresponding decreases in the amount of mercury required for adequate amalgamation.

EXAMPLE II

This example was carried out to determine the variation in the 24 hour compressive strength of the amalgam when the amount of indium was varied in the powder composite. A conventional-type, silver-tin base alloy powder was admixed with 0% to 20% indium powder to prepare the powder composites. The amalgams were prepared by triturating the powder composite sampled for 20 seconds employing a low energy input amalgamator, condensing the amalgams at 10,000 psi and aging for 24 hours at room temperature.

| Sample No. | Weight Indium % | Mercury to Composite Weight Ratio | 24 Hour Compressive Strength-psi |
|---|---|---|---|
| 7 | 0 | 0.75:1 | 41,900 |
| 8 | 5 | 0.75:1 | 62,400 |
| 9 | 10 | 0.75:1 | 72,000 |
| 10 | 15 | 0.75:1 | 61,200 |
| 11 | 20 | 0.75:1 | 37,400 |

The above data show that the compressive strength of conventional-type amalgams are increased by up to 30% by the addition of indium and the corresponding decrease in mercury. Maximum strength occurs at an indium level of about 10% by weight in the powder composite for the particular alloy type and method of preparation used in the above Example.

EXAMPLE III

This example was carried out to determine and compare the effect of indium on the 24 hour compressive strength of amalgams prepared by admixing one of two different commercial, silver-tin base, alloy powders (designated A and B) with indium powder in preparing the powder composites. The amalgams were prepared by triturating the powder composite samples for 20 seconds employing a low energy amalgamator, condensing the amalgam at 10,000 psi and aging for 24 hours at room temperature. The mercury to composite weight ratio used was 1:1 for all samples in this test, and all samples expressed considerable residual mercury on condensation.

| Sample No. | Weight Indium % | 24 Hour Compressive Strength, psi A | D |
|---|---|---|---|
| 12 | 5 | 60,000 | 60,500 |
| 13 | 10 | 62,800 | 66,500 |
| 14 | 15 | 61,400 | 67,700 |
| 15 | 20 | 57,200 | 68,400 |

The above data show that the optimum indium concentration for compressive strength depends on the specific silver-tin alloy powder used in the powder composite. Using commercial alloy powder A the optimum indium content is approximately 10% by weight, while for B the compressive strength is still climbing at 20% indium by weight. The difference may be attributed to the composition and/or particle size and distribution differences between the two commercial alloy powders.

EXAMPLE IV

This example was carried out to determine the effect of the indium addition on the 24 hour compressive strength of dispersion-type amalgam filling materials such as that disclosed in my U.S. Pat. No. 3,305,356 issued Feb. 21, 1967. The powder composite was prepared by adding indium powder to a dispersion-type alloy powder base, the latter being comprised primarily of a silver-tin base alloy powder admixed with a silver-copper alloy dispersion powder, said dispersion alloy containing about 72% by weight silver and about 28% by weight copper. The amalgam samples were prepared by triturating the powder composite for 10 seconds in a high energy imput amalgamator, condensing the amalgam at 10.000 psi and aging for 24 hours at room temperature.

| Sample No. | Weight Indium % | Mercury to Composite Weight Ratio | 24 Hour Compressive Strength-psi |
|---|---|---|---|
| 16 | 0 | 1:1 | 52,300 |
| 17 | 5 | 0.75:1 | 60,800 |
| 18 | 10 | 0.75:1 | 62,900 |

The above data show that the compressive strength of a dispersion-type amalgam filling material is increased by about 20% by the incorporation of indium into the amalgam in the amounts shown with correspondingly decreasing amounts of mercury required for amalgamation.

The dispersion-type amalgam as disclosed in my aforementioned U.S. Patent may be formed from an alloy powder composite of (a) about 50% to about 95% by weight of an amalgamatable alloy in powder form consisting essentially of 75% by weight silver and 25% by weight tin, said alloy having up to 8% by weight of the silver-tin alloy replaced by up to 6% by weight of copper and up to 2% by weight of zinc and (b) about 5 to about 50% by weight of discrete particles of a substantially non-amalgamatable alloy containing at least 50% by weight of silver, the substantially non-amalgamatable alloy is of a substantially different chemical composition from the amalgamatable alloy and is present as a dispersion phase in the amalgam matrix in the form of discrete particles remaining essentially intact in the set amalgam.

EXAMPLE V

This example was carried out to show the variation in compressive strength of the dispersion-type amalgam when the amount of dispersion phase is varied for a fixed indium content. The powder composite samples were prepared by adding 10% by weight of indium powder to a dispersion-type alloy powder, the latter being comprised of a silver-tin base alloy powder admixed with varying amounts of a dispersion alloy powder, said dispersion alloy containing about 72% by weight silver and about 28% by weight copper and of particle size −400 mesh. The amalgam samples were prepared by triturating the powder composite for 12.5 seconds in a high energy imput amalgamator, condensing the amalgams at 10,000 psi, and aging for 1 hour and 24 hours at room temperature. The mercury to composite weight ratio used for trituration was 0.75:1 in each case.

| Sample No. | Weight Indium % | Weight Dispersion Alloy % | Compressive Strength, psi 1 Hour | 24 Hour |
|---|---|---|---|---|
| 19 | 10 | 33 | 19,500 | 62,900 |
| 20 | 10 | 42 | 25,600 | 82,200 |
| 21 | 10 | 50 | 21,000 | 62,500 |

The above data show that when the powder composite contains about 10% by weight indium, the optimum amount of dispersion phase alloy powder is about 42% by weight in the powder composite. Compared to the dispersion-type amalgam containing no indium (sample no. 16) sample no. 20 shows approximately a 55% increase in compressive strength. Also, the high 1 hour strength indicates a relatively fast setting rate.

EXAMPLE VI

This example was carried out to determine the effect of the presence of indium on the dimensional change resulting on the setting of the amalgam. Two commercial-type alloys were used, (A) a conventional silver-tin base alloy such as that used in the previous examples I, II, and III, and (B) a dispersion-type alloy such as that employed in Example IV. Indium powder was admixed with each to form composite samples 23 and 25. The amalgam samples were prepared by triturating the alloy powders and their respective composites containing indium for 10 seconds in a high energy imput amalgamator and condensing at 10,000 psi. The dimensional changes were determined in accordance with ADA specification 4.3.4.

| Sample No. | Composite | Mercury to Composite Weight Ratio | 24 Hour Dimensional Changes % |
|---|---|---|---|
| 22 | A | 1:1 | −0.03 |
| 23 | A + 10% indium | 0.75:1 | −0.02 |
| 24 | B | 1:1 | 0.00 |
| 25 | B + 10% indium | 0.75:1 | +0.003 |

The above data show that incorporation of indium into an amalgam tends to diminish contraction or slightly enhance expansion during setting of amalgam.

I claim:

1. A dental powder composite adapted to be combined with mercury to form dental amalgam comprising:
   a. about 70% to about 99.5% by weight of an amalgamatable alloy in powder form of about 75% by weight silver and about 25% by weight tin, said alloy having up to about 8% by weight of the silver-tin alloy replaced with up to about 6% by weight of copper and up to about 2% by weight of zinc, and
   b. about 0.5% to less than 30% by weight of unalloyed indium powder.

2. A dental powder composite as in claim 1 wherein said amalgamatable alloy comprises from about 85% to about 95% by weight of the composite and wherein said unalloyed indium powder comprises from about 5% to about 15% by weight of the composite.

3. The dental powder composite of claim 1 combined with mercury in the form of an amalgam.

4. The dental amalgam of claim 3 wherein the mercury is present in a weight ratio of mercury to composite from 0.5:1 to 1:1.

5. The dental amalgam of claim 3 wherein the mercury is present in a weight ratio of mercury to composite from about 0.5:1 to about 0.75:1.

6. A dental powder composite adapted to be combined with mercury to form dental amalgam comprising:
   a. about 70% to about 99.5% by weight of (i) about 50% to about 95% by weight of an amalgamatable alloy in powder form of about 75% by weight silver and about 25% by weight tin, said alloy having up to about 8% by weight of the silver-tin alloy replaced with up to about 6% by weight of copper and up to about 2% by weight of zinc, and (ii) about 5% to about 50% by weight of discrete particles of a substantially non-amalgamatable alloy containing at least 50% by weight silver, said substantially non-amalgamatable alloy being of substantially different chemical composition from said amalgamatable alloy and present as a dispersion phase in a subsequently formed amalgam matrix, and
   b. about 0.5% to less than 30% by weight of unalloyed indium powder.

7. A dental powder composite as in claim 6 which comprises:
   a. from about 85% to about 95% by weight of said amalgamatable alloy and said unamalgamatable alloy; and
   b. from about 5% to about 15% by weight of said unalloyed indium.

8. The dental powder composite of claim 6 combined with mercury in the preparation of an amalgam filling material.

9. The amalgam filling material of claim 8 wherein the mercury is present in a weight ratio of mercury to composite from 0.5:1 to 1:1.

10. The amalgam filling material of claim 8 wherein the mercury is present in a weight ratio of mercury to composite from about 0.5:1 to about 0.75:1.

11. The amalgam filling material of claim 8 wherein the substantially non-amalgamatable alloy is in the form of discrete particles in the amalgam.

12. The amalgam filling material of claim 9 wherein the substantially non-amalgamatable alloy is in the form of discrete particles in the amalgam.

13. The amalgam filling material of claim 10 wherein the substantially non-amalgamatable alloy is in the form of discrete particles in the amalgam.

14. The dental powder composite of claim 6 wherein said substantially non-amalgamatable alloy consists essentially of a silver-copper alloy containing at least 50% by weight silver and the remainder copper.

15. The dental powder composite of claim 6 wherein said substantially non-amalgamatable alloy consists essentially of a silver-copper eutectic alloy consisting essentially of about 72% by weight silver and about 28% by weight of copper.

16. The dental powder composite of claim 14 combined with mercury in the preparation of amalgam filling material.

17. The amalgam filling material of claim 16 wherein the mercury is present in a weight ratio of mercury to composite from 0.5:1 to 0.75:1.

18. The dental powder composite of claim 15 combined with mercury in the preparation of an amalgam filling material.

19. The amalgam filling material of claim 18 wherein the mercury is present in a weight ratio of mercury to composite from 0.5:1 to 0.75:1.

20. The dental powder composite of claim 6 comprising:
   a. about 45% to 50% by weight of said amalgamatable alloy powder,
   b. about 40% to 45% by weight of said substantially non-amalgamatable alloy powder, and
   c. about 8% to 12% by weight of said unalloyed indium powder.

21. The dental powder composite of claim 6 comprising:
   a. about 48% by weight of said amalgamatable alloy powder,
   b. about 42% by weight of said substantially nonamalgamatable alloy powder, and
   c. about 10% by weight of said unalloyed indium powder.

22. The dental powder composite of claim 20 wherein said substantially non-amalgamatable silver base alloy is comprised of about 75% by weight silver and about 28% by weight copper.

23. The dental powder composite of claim 20 combined with mercury in the preparation of an amalgam filling material.

24. The amalgam filling material of claim 23 wherein the mercury is present in a weight ratio of mercury to composite from 0.5:1 to 0.75:1.

25. The dental powder composite of claim 22 combined with mercury in the preparation of an amalgam filling material.

26. The amalgam filling material of claim 25 wherein the mercury is present in a weight ratio of mercury to composite from about 0.5:1 to 0.75:1.

* * * * *